US007068816B1

(12) United States Patent
Knoblauch et al.

(10) Patent No.: US 7,068,816 B1
(45) Date of Patent: Jun. 27, 2006

(54) METHOD FOR USING REMOTELY SENSED DATA TO PROVIDE AGRICULTURAL INFORMATION

(75) Inventors: Gregory E. Knoblauch, Aurora, CO (US); Andrew P. Dinville, Arvada, CO (US); Jack F. Paris, Longmont, CO (US)

(73) Assignee: DigitalGlobe, Inc., Longmont, CO (US)

( * ) Notice: Subject to any disclaimer, the term of this patent is extended or adjusted under 35 U.S.C. 154(b) by 634 days.

(21) Appl. No.: 10/047,423

(22) Filed: Jan. 15, 2002

(51) Int. Cl.
*G06K 9/00* (2006.01)

(52) U.S. Cl. .......................... 382/110; 382/100; 702/5; 348/89; 348/144

(58) Field of Classification Search ................ 382/100, 382/103, 110; 348/89, 144; 702/5
See application file for complete search history.

(56) References Cited

U.S. PATENT DOCUMENTS

| 5,878,356 | A | 3/1999 | Garrot, Jr. et al. ............... 701/1 |
| 6,029,106 | A | 2/2000 | Hale et al. ...................... 701/50 |
| 6,178,253 | B1 * | 1/2001 | Hendrickson et al. ...... 382/110 |
| 6,236,907 | B1 * | 5/2001 | Hauwiller et al. .......... 700/283 |
| 6,366,681 | B1 * | 4/2002 | Hutchins .................... 382/110 |
| 6,421,610 | B1 * | 7/2002 | Carroll et al. ................. 702/5 |

OTHER PUBLICATIONS

Baret, F., and G. Guyot, "Potentials and Limits of Vegetation Indices for LAI and APAR Assessment", 35:161-173, 1991, Remote Sensing of Environment.

Baret, F. and G. Guyot, and D. Major, "TSAVI: a Vegetation Index Which Minimizes Soil Brightness Effects on LAI and APAR Estimation", pp. 1355-1358, Jul. 10-14, 1989, 12th Canadian Symposium on Remote Sensing and IGARSS'90, Vancouver, Canada.

Elvidge, C.D., and Z. Chen, "Comparison of Broad-band and Narrow-band Red and Near-infrared Vegetation Indices", 54:38-48, 1995, Remote Sensing Environment.

Epiphanio, J.C.N., and A.R. Huete, "Dependence of NDVI and SAVI on Sun/Sensor Geometry and Its Effect on fAPAR Relationships in Alfalfa", 51:351-360, 1995, Remote Sensing of Environment.

Huete, A., "A Soil-adjusted Vegetation Index (SAVI)", 25:295-309, 1988, Remote Sensing of Environment.

(Continued)

*Primary Examiner*—Bhavesh M. Mehta
*Assistant Examiner*—John Strege
(74) *Attorney, Agent, or Firm*—Holland & Hart LLP; Christopher J. Kulish, Esq.

(57) ABSTRACT

The present invention is directed to a method for producing agricultural information on an area of interest, with the information based on raw, remote imaging data that is typically produced by a sensor associated with a satellite or aircraft. In one embodiment, the method includes processing raw, remote imaging data to produce reflectance factor data on the land of interest. The reflectance factor data is then used to produce agriculturally significant information. In one embodiment, a soil zone index map is produced for the land of interest. In another embodiment, the reflectance factor data is used to produce a green vegetation index map. In yet a further embodiment, the reflectance factor data at two points in time is used to produce a map for the land of interest that indicates the change in the green vegetation index over time.

31 Claims, 6 Drawing Sheets

OTHER PUBLICATIONS

Huete, A., R.D. Jackson, and D.F. Post, "Spectral Response of Plant Canopy With Different Soil Backgrounds", 17:37-53, 1985, Remote Sensing of Environment.

Huete A., C. Justice, and H. Liu, "Development of Vegetation and Soil Indices for MODIS-EOS", 49:224-234, 1994, Remote Sensing of Environment.

Huete, A.R., H.Q. Liu, K. Batchily, and W. van Leeuwen, "A Comparison of Vegetation Indices Over a Global Set of TM Images for EOS-MODIS", 59:440-451, 1997, Remote Sensing of Environment.

Moran, M.S., Y. Inoue, and E.M. Barnes, "Opportunities and Limitations for Image-based Remote Sensing in Precision Crop Management", 61:319-346, 1997, Remote Sensing of Environment.

Myneni, R.B., S. Maggion, J. Iaquinta, J.L. Privette, N. Gobron, B. Pinty, D.S. Kimes, M.M. Verstraete, and D.L. Williams, "Optical Remote Sensing of Vegetation: Modeling, Caveats, and Algorithms", 51:169-188, 1995, Remote Sensing of Environment.

Paris, J.F., "TNTmips Project Workbook: From Start to Finish!", 219 pp., 1999, 3rd Ed., Paris & Associates, Inc., #255, 1172 S. Main Street, Salinas, CA 93901.

Perry, C.R., Jr., and L.F. Lautenschlager, "Functional Equivalence of Spectral Vegetation Indices", 14:169-182, 1984, Remote Sensing of Environment.

Price, J.C., "Estimating Vegetation Amount from Visible and Near Infrared Reflectances", 41:29-34, 1992, Remote Sensing of Environment.

Qi, J., A. Chehbouni, A.R. Huete, Y.H. Kerr, and S. Sorooshian, "A Modified Soil Adjusted Vegetation Index", 48:119-126, 1994, Remote Sensing of Environment.

Rondeaux, G., M. Steven, and F. Baret, "Optimization of Soil-Adjusted Vegetation Indices", 55:95-107, 1996, Remote Sensing of Environment.

Rouse, J.W., R.H. Haas, J.A. Schell, and D.W. Deering, "Monitoring Vegetation Systems in the Great Plains With ERTS", 309-317, 1973, In 3rd ERTS Symposium, NASA SP-351, NASA, Washington, DC, vol. 1.

Wiegand, C.L., A.J. Richardson, D.E. Ecobar, and A.H. Gerbermann, "Vegetation Indices in Crop Assessments", 35:105-119, 1991, Remote Sensing of Environment.

Moran, M.S., R. Bryant, K. Thome, W. Ni, Y. Nouvellon, M.P. Gonzalez-Dugo, J. Qi, T.R. Clarke, A Refined Empirical Line Approach for Reflectance Factor Retrieval from Lansat-5 TM and Landsat-7 ETM+, 78:71-82, 2001, Remote Sensing of Environment.

* cited by examiner

METHOD FOR USING REMOTELY SENSED DATA TO PROVIDE AGRICULTURAL INFORMATION

FIELD OF THE INVENTION

The present invention is directed to a method for providing agriculture information on an area of interest, with the agricultural information being derived from the raw image data produced by a remote sensor associated with a remote sensing platform.

BACKGROUND OF THE INVENTION

The profit margins associated with the production and marketing of many crops have been generally decreasing for a number of years. This decrease in profit margins has caused many of the producers in the industry to turn to technology for information that facilitates the management of the crop producing land to increase the yield and/or reduce losses due to disease, drought and the like.

Presently, one method for producing crop related information that allows the producers to manage crop producing land is to use remote sensing platforms (e.g., aircraft, satellites, and land vehicles) that are equipped with sensors that allow raw image data to be collected on the agricultural land of interest as the platform passes over the land. Typically, the raw image data is from one or more discrete bands in the electromagnetic spectrum that are capable of yielding agricultural information. For instance, an indication of the amount of chlorophyll in a plant may manifest itself in the "light" sensed from the land of interest in one or a combination of bands. This raw image data for the land of interest is subsequently processed to produce maps that provide the producers with information that can be utilized to manage crop production. For instance, a map that shows chlorophyll concentrations over the area of interest could be used by a producer to identify portions of the land that are under producing relative to other portions of the land and take appropriate action.

SUMMARY OF THE INVENTION

The present invention has recognized that much, if not all, of the agricultural information produced from the raw image data collected by remote sensing platforms is subject to sensor and/or atmospheric effects that lead to inconsistent data from one area of interest to another area or interest, from one sensor to another sensor, and/or from one time to the next time.

The present invention reduces the adverse effects of the sensor and/or atmosphere so that more consistent agricultural information is produced thereby rendering the information easier for producers and others in the agricultural industry to utilize. In other words, the invention produces more consistent agricultural information between different areas of interest. Consequently, if a producer has two different areas of land that are each planted with the same crop, a particular type of agricultural information produced by the invention on each of the two areas is substantially consistently represented, thereby facilitating the producers ability to compare the two crops to one another.

In one embodiment, the present invention includes the steps of receiving information that defines the area of interest of the recipient of the agricultural information and receiving remote imaging data on the area of interest. The remote imaging data or raw data, which is typically produced by a sensor associated with a satellite or aircraft, is processed to produce reflectance factor data on the area of interest. To elaborate, the raw data is subject to effects that skew information on the area of interest. For example, the atmosphere between the area of interest and the sensor, whether satellite or aircraft based, if not taken into account, skews the agricultural information on the area of interest. By processing the raw data to produce reflectance factor data, the effects of the atmosphere and/or other sources of skewing or error are significantly reduced. The method further involves using the reflectance factor data to produce agricultural information on the area of interest. In one embodiment, the reflectance factor data is produced using agricultural scene objects.

In one embodiment, the agricultural information is a green vegetation index (GVI) pixel map of the area of interest that provides an objective measure of the vegetation canopy. Each pixel on the map represents a particular portion of the area of interest. For instance, a pixel can represent a 5m by 5m area within the area of interest. In one embodiment, the pixel map utilizes colors to indicate the GVI for the portion of the area of interest represented by each pixel. For example, brown can represent no vegetation, dark green can represent the densest vegetation canopy, and other colors can be used to represent canopies between these two extremes.

In another embodiment of the invention, the agricultural information is a pixel map that indicates changes in the GVI from date to date. Each pixel in the map is capable of representing a negative change, positive change or no change. The changes or lack of change associated with the land that each pixel represents are, in one embodiment, represented by colors. For example, shades of yellows and red can be used to represent negative changes in the GVI between two dates, shades of blue and green can be used to represent positive changes in GVI between two dates, and white can be used to represent no change in GVI between two dates. In one embodiment, the dates on which GVI information is produced that can be utilized to produce the map are within a week of each other. Consequently, the entity requesting the map is able to monitor changes between GVI maps on at least a weekly basis and potentially on a more frequent basis, such as day to day.

In a further embodiment of the invention, the agricultural information is a vegetation index map other than a GVI map, such a map of the Difference Green Vegetation Index (DGVI), Perpendicular Green Vegetation Index (PGVI), Normalized Difference Vegetation Index (NDVI), Simple Ratio Vegetation Index (SRVI), Infrared Percentage Vegetation Index (IRPVI), Soil Adjusted Vegetation Index (SAVI), Transformed Soil Adjusted Vegetation Index (TSAVI), Modified SAVI (MSAVI), or MSAVI2. Another embodiment applies the reflectance factor data to produce two such maps that relate to different times and are used to generate a difference or change map.

In yet a further embodiment of the invention, the agricultural information is a soil zone index (SZI) pixel map that characterizes an agricultural area of interest in terms of relative soil properties. In one embodiment, the relative soil properties that are characterized are a combination of surface soil wetness, soil texture, and organic matter content. The SZI map is considered most applicable to bare or mostly bare fields and is most likely to be utilized in making decisions regarding crop planning and management.

In yet another embodiment of the invention, the agricultural information is a soil index map other than the SZI map, such as a map of the Soil Brightness Index.

Another aspect of the invention involves the conveyance of the agricultural information produced from the reflectance factor data. To elaborate, the pixel map is typically produced and stored in a digital format that can be transmitted to the entity that requested the agricultural information. In one embodiment, the map is transmitted to the requesting entity over the Internet. It is also feasible to record the map on a magnetic disk, CD, tape or other recording medium and then send the recorded medium to the requesting entity.

DETAILED DESCRIPTION

Generally, the present invention is directed to the production of agricultural information that is correlated to an area of interest (AOI), which is typically one or more fields. The process involved in producing the agricultural information includes receiving information that identifies the AOI, which is typically provided by the entity requesting the information. Also included in the process is receiving raw imaging data on the area of interest from which agricultural information on the AOI can be derived. The raw data is processed to produce reflectance factor data, thereby substantially reducing the skewing effects attributable to the atmosphere and the sensor used to produce the data. The reflectance factor data is further processed to produce agricultural information that is correlated to the AOI.

Figure 1:
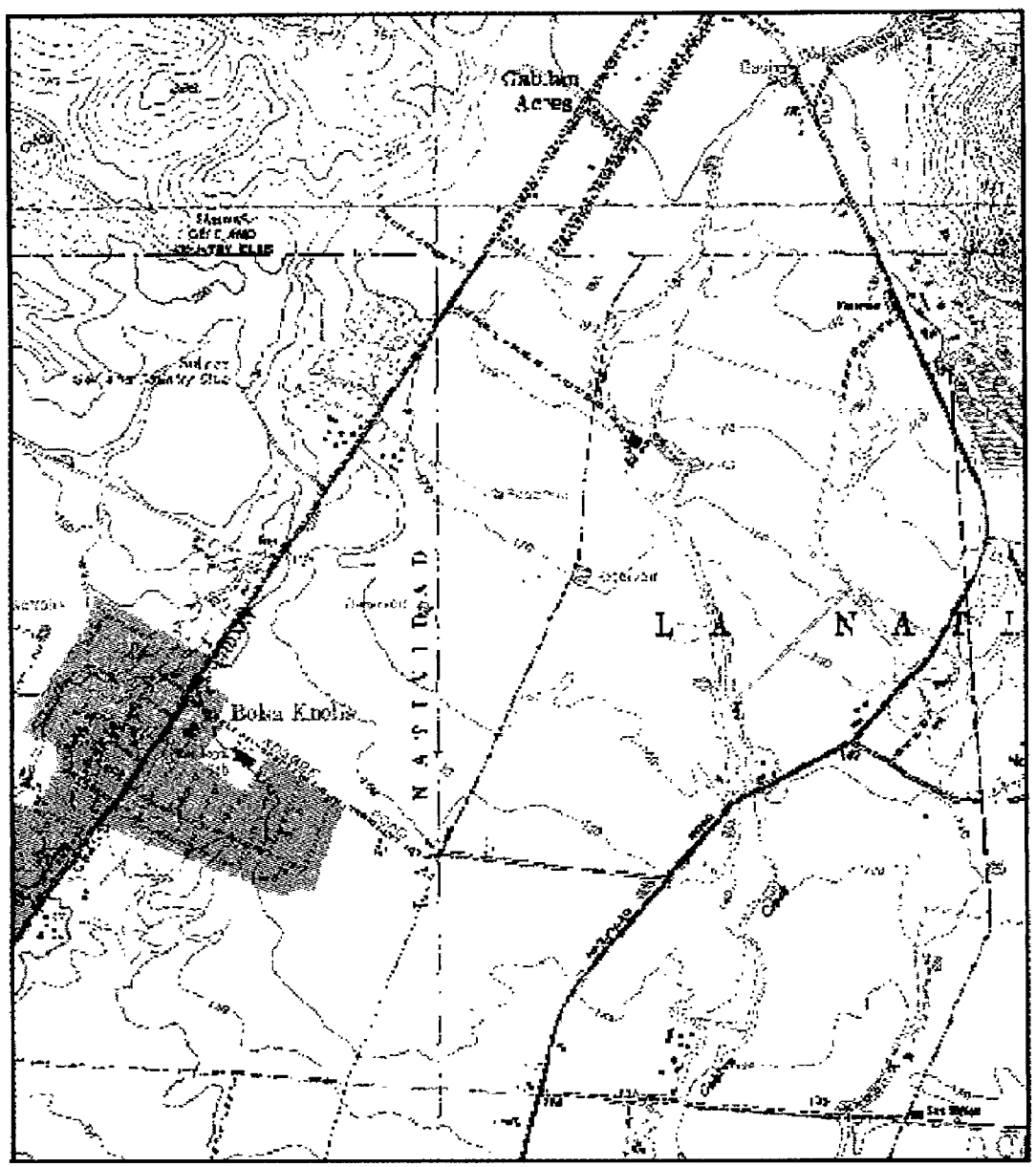
FIG. 1 illustrates a digital topographic map in which an area of interest (AOI) is located.

Having generally described the process for producing the agricultural information, an embodiment of the process is described in greater detail. To provide agricultural information on an AOI, the AOI is identified in a manner that allows the agricultural information that is to be subsequently produced to be correlated with the AOI. One way to identify the AOI is to have the requester specify the boundaries of the AOI in terms of latitude and longitude. Specifying the AOI in this manner may be cumbersome for a requester. Consequently, to facilitate the identification of the AOI, the requester is provided with tools that facilitate the identification of the AOI. Typically, the tools are in the form of software that a requester can load onto a computer system. For AOIs in the United States, the tools include a digital topographic map product that is in the form of a digital raster of the USGS map(s) that encompass the AOI. The USGS maps generally provide landmarks (roads, cities, waterways etc.) and township, range, and section information that is useful in identifying the AOI. An example of a topographic map product that encompasses an area of interest is shown in FIG. 1. It should be appreciated that the process is adaptable to maps other than USGS maps, provided the maps are capable of being correlated with the mapping information that is associated with the raw data.

Figure 2:
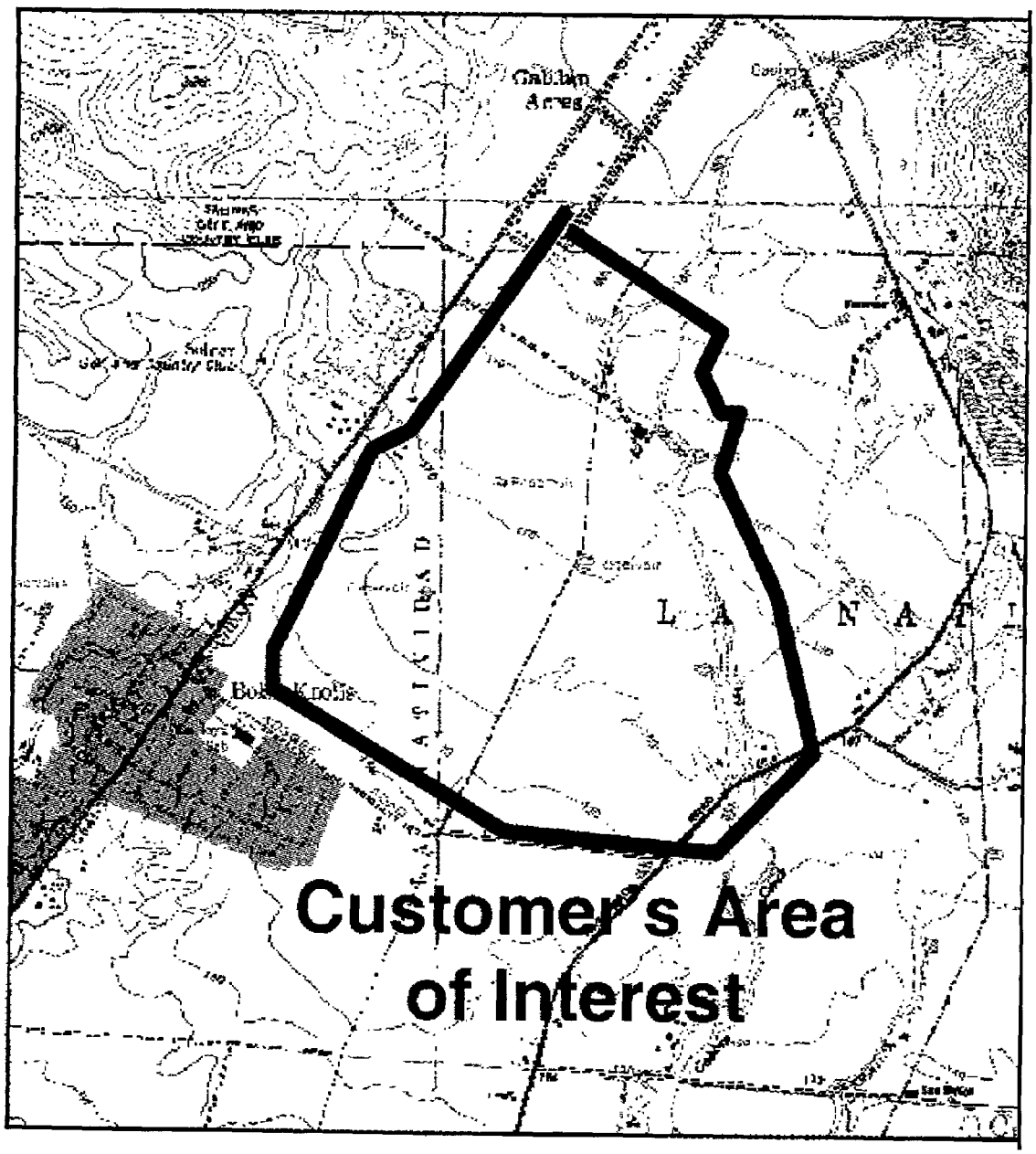
FIG. 2 illustrate the digital topographic map of FIG. 1 with an overlying polygon that identifies the boundaries of the AOI within the area shown by the digital topographic map.
Figure 3:
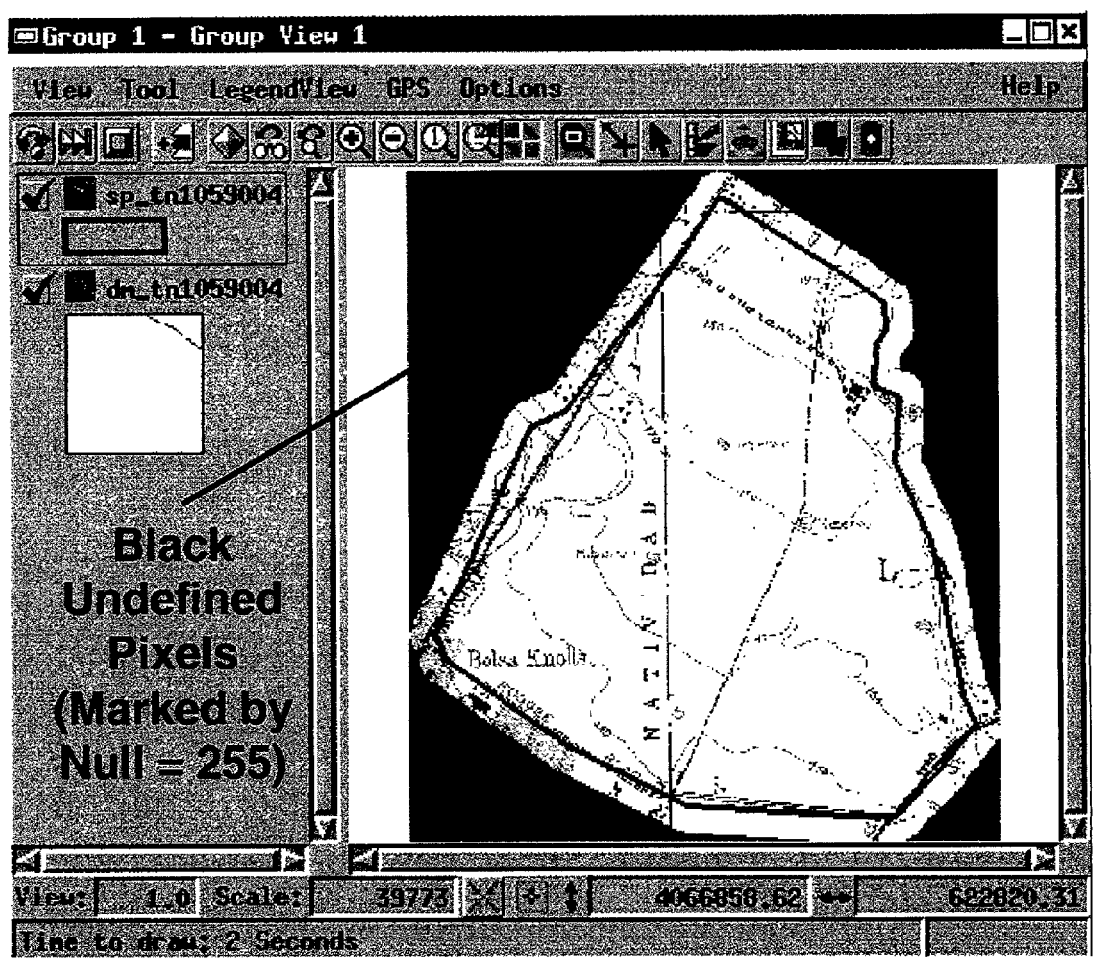
FIG. 3 illustrates the digital topographic map of FIG. 1 with the overlying polygon that identifies the AOI, as displayed on a video monitor.

The requester is also provided with an area polygon product for producing a vector data layer that allows the requester to delineate the AOI relative to the topographic map. Stated differently, the area polygon product allows the requester to create a polygon that defines the AOI relative to the topographic map by producing an overlay to the topographic map that delineates the AOI. An example of a topographic map with overlying polygon that delineates the boundaries of an AOI is shown in FIG. 2. With respect to AOIs in the U.S., the requester is able to produce the polygon defining an AOI that is a section of land by specifying the township, range and section. The process is adaptable to other schemes for identifying parcels of land utilized in other countries. FIG. 3 illustrates the digital topographic map of FIG. 1 with the overlying polygon that identifies the AOI, as displayed on a video monitor.

Figure 4:
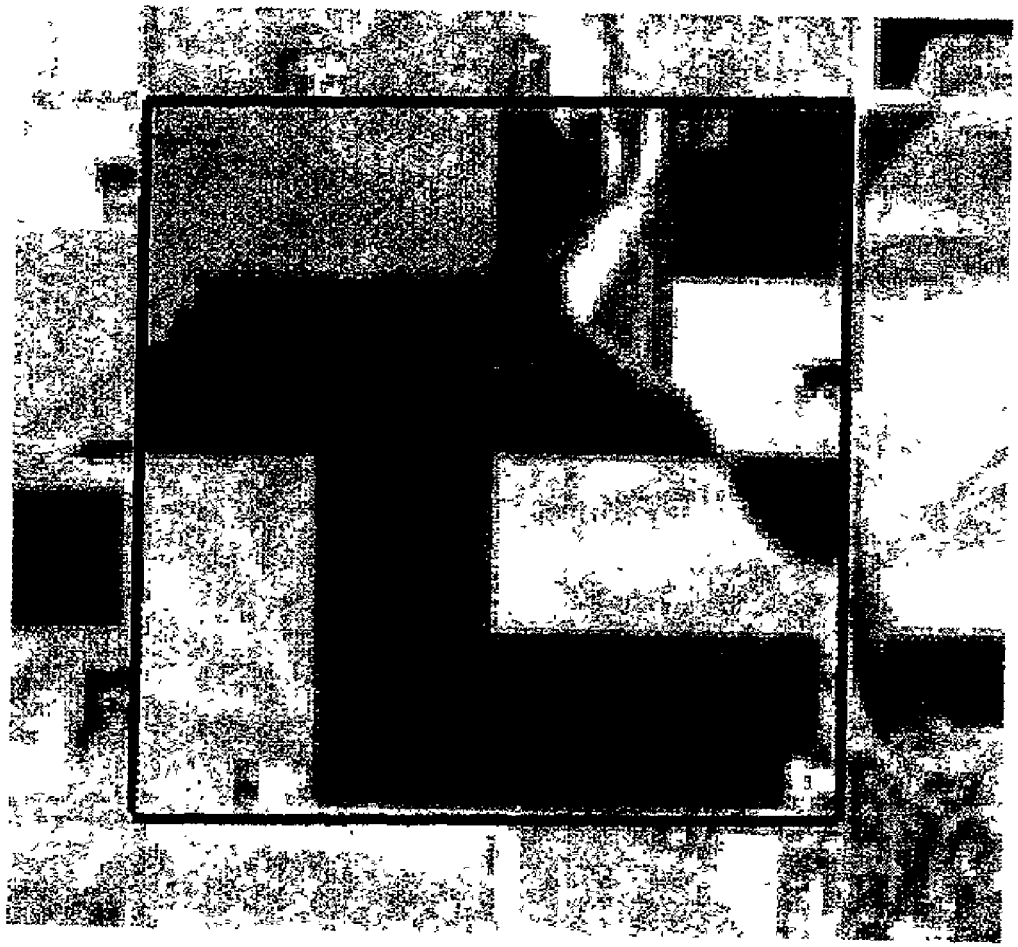
FIG. 4 shows a panchromatic image of field an AOI that is a section of land with a number of fields.

Once an AOI is identified, the requester is further provided with a pan image product that is a panchromatic (black and white) image of the AOI. This image is typically utilized by the requester to facilitate the identification of fields within an AOI in the maps that are produced from the raw data and provide agricultural information on the AOI. FIG. 4 is an example of a panchromatic image that includes an AOI in the form of a section of land with a number of fields.

A sensor, typically associated with a satellite or aircraft, produces raw image data or raw image raster values ($RV_b$) for each of the spectral bands that are needed to produce the agricultural information for the AOI. More specifically, the sensor produces a raw image raster value for each of the electromagnetic bands of interest for each pixel in the scene (i.e., the area being viewed by the sensor) that includes the AOI. In one embodiment, the sensor is capable of producing raw image raster values a blue light band, green light band, red light band and near infra-red band, which are also respectively referred to as band 1, band 2, band 3 and band 4. It should also be appreciated that raw image raster values for a greater or lesser number of spectral bands may be required to produce a particular type of agricultural information.

Figure 5:
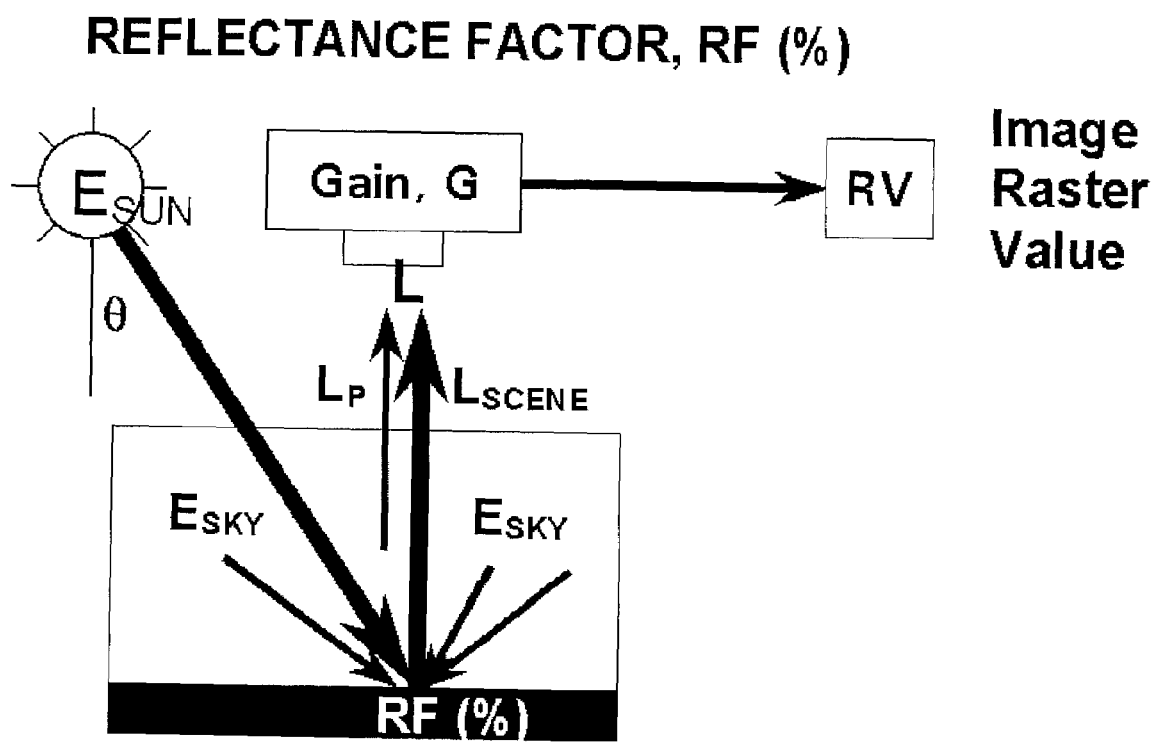
FIG. 5 illustrates the relationship of solar and atmospheric irradiances on the spectral radiance observed by a sensor directed at the earth's surface.
Figure 6:
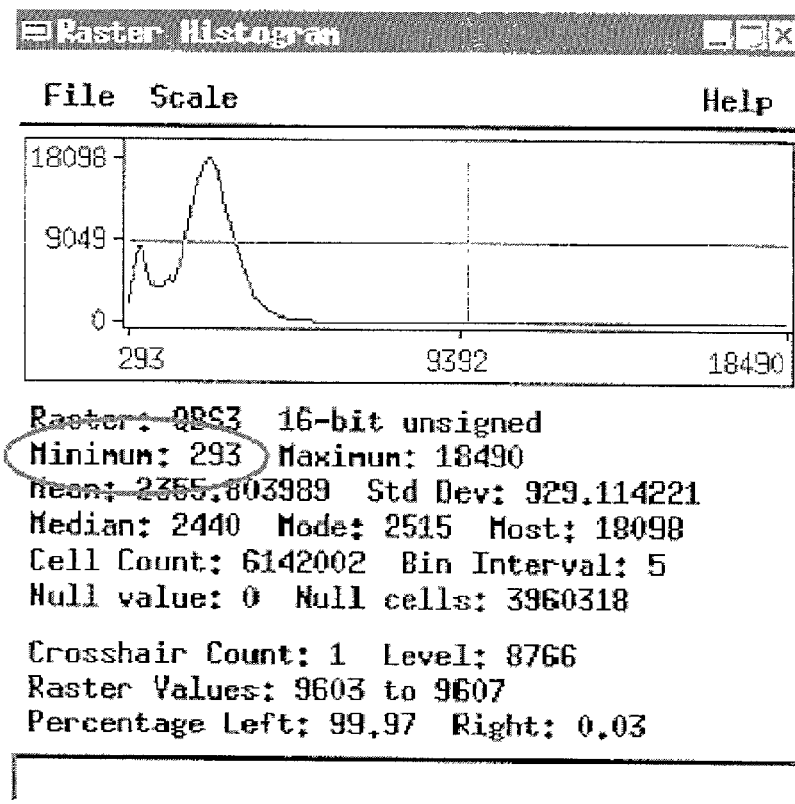
FIG. 6 illustrates a print out of a raster histogram tool that is capable of identifying a pixel in a radiance image that has a reflectance factor of effectively zero.
Figure 6:
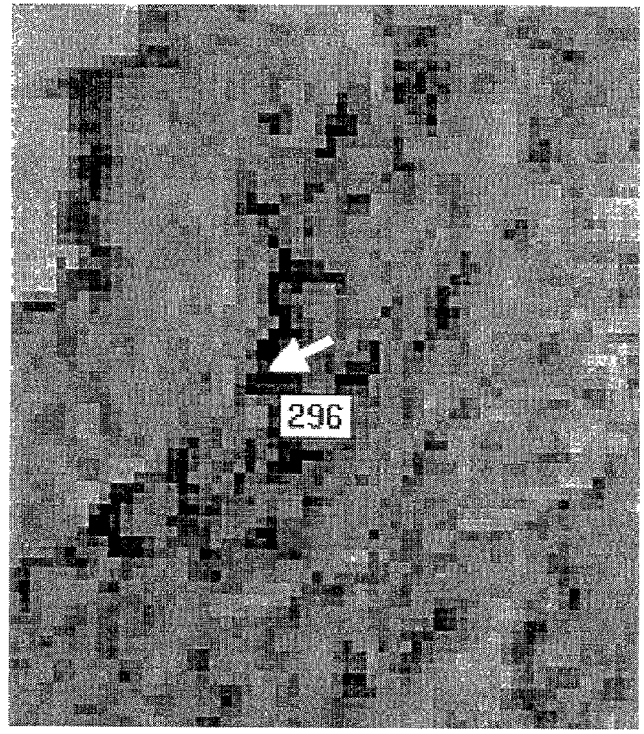

The raw image raster values for each band for each pixel that relates to the AOI is subjected to a sensor/radiance calibration step. For simplicity, the calibration is described with respect to the raw image raster value for a single pixel associated with a single band with the understanding that the production of certain agricultural information will require the processing of raw image raster values associates with multiple bands and multiple pixels. With reference to FIG. 5, the raster value associated with a pixel is represented by the following equation:

$$RV_b = G_b(x,y,t,L_b)L_b \tag{1}$$

where $RV_b$ is the raw image raster value for a band b for a pixel, $G_b$ is the gain of the sensor for band b and varies over the images extent (x,y), over time (t), and perhaps with respect to the level of the spectral radiance being sensed ($L_b$). $G_b$ also includes the effects of other sensor parameters, such as instantaneous field of view, and modulation transfer function. For simplicity, the function $G_b(x, y, t, L_b)$ is hereinafter referred to simply as $G_b$ with the dependencies implied. Equation (1) can be rewritten as:

$$L_b = RV_b/G_b \tag{2}$$

Spectral radiance calibration of the $RV_b$ data is achieved by application of equation (2) to the $RV_b$ data, namely, dividing the $RV_b$ data by the value of $G_b$, which is known value for a given sensor. The application of equation (2) to each pixel of an image for a particular spectral band produces a radiance image.

The radiance image data is also commonly subject to positional or geometric skewing in terms of a given map coordinate system projection (mapping system and datum). Such skewing is or can be due to many factors (e.g., distortion in the camera system associated with the sensor, a tilt in the imaging system etc.). Correction involves the shifting of the pixels in the raster so that there is a substantially uniform distribution of pixels across the radiance image of the AOI in terms of the map coordinates of some selected mapping system and datum. If the data is subject to geometrical skewing, the data should be corrected so that the resulting map embodying the agricultural information conforms to the mapping system being utilized by the requester. Otherwise the resulting map may be very difficult for the requester to recognize as relating to the AOI. Such corrections to image data, such as radiance image data, are well-known in the art and, as a consequence, will not be elaborated upon further.

After the raw image raster values ($RV_b$) for the pixels in an image of the AOI and for each relevant band have been subjected to sensor/radiance calibration and/or correction for geometric skewing, atmospheric correction/reflectance calibration is performed on the radiance data $L_b$. As shown in FIG. 5, the total radiance encountered by the sensors is sum of two additive streams of radiant energy and can be represented as:

$$L_b = L_{pb} + L_{sb} \tag{3}$$

where $L_b$ is the total spectral radiance measured by the sensor, $L_{pb}$ is the spectral radiance attributable to the scattering of electromagnetic radiation by gases and other materials in the atmosphere between the sensor and the surface of the earth; and $L_{sb}$ is the spectral radiance attributable to diffuse reflectance by surface materials, such as soils and crops. Equation (3) is rewritten to solve for the $L_{sb}$ term, which relates to the soils and vegetation that are of interest, as follows:

$$L_{sb} = L_b - L_{pb} \tag{4}$$

Equation (3) can be represented by the following equation:

$$L_b = \frac{(E_b t_{sb} \cos\theta + E_{b,sky})t_{0b}}{\pi} RF_b + L_{pb} \tag{5}$$

where $E_b$ is the spectral irradiance of the sun at the top of the atmosphere for band b; $t_{sb}$ is band transmittance (with the subscript s referring to the transmission loss between the sun and the surface of the earth); $\theta$ is solar zenith angle; $E_{b,sky}$ is the diffuse sky irradiance; $T_{0b}$ is the transmittance of the atmosphere between the surface of the earth and the sensor; and $RF_b$ is the reflectance factor for band b. Equation (5) applies to surfaces with Lambertian reflectance characteristics. Agricultural surfaces, however, have been found to exhibit non-Lambertian reflectance characteristics. This anisotropic behavior is addressed by replacing $RF_b$ with a bidirectional reflectance factor $BRF_b$. Alternatively, $RF_b$ and $\pi$ can be replaced with the bidirectional reflectance distribution factor $BRDF_b$. The term $RF_b$ is retained hereinafter with the understanding that it refers to $BRF_b$. To solve for $RF_b$, equation (5) is rewritten as follows:

$$RF_b = \frac{\pi(L_b - L_{pb})}{(E_b t_{sb}\cos\theta + E_{b,sky})t_{0b}} \tag{6}$$

Equation (6) can be simplified to the following:

$$RF_b = (L_b - L_{pb})m_b \tag{7A}$$

where $m_b = \pi/(E_b t_{sb} \cos\theta + E_{b,sky})t_{0b}$ \hfill (7B)

It is unlikely that all of the atmospheric parameters associated with $m_b$ and embodied in equation (7B) would be known as a sensor surveys a particular scene. However, the linear nature of equation (7A) implies that only two independent items of information are needed about the surface reflectance within the scene to determine $L_{pb}$ and $m_b$. Specifically, if a dark object and a bright object can be found in the pixels of the radiance images with known reflectance factors, the two unknowns of equation (7A), $L_{pb}$ and $m_b$, can be determined and the equation solved for $RF_b$. To elaborate, if the known reflectance factor of the bright object is $RF_{b,bright}$ and the known reflectance factor for the dark object is $RF_{b,dark}$ and the observed radiances for the bright object and dark object are respectively, $L_{b,bright}$ and $L_{b,dark}$, then:

$$m_b = (RF_{b,bright} - RF_{b,dark})/(L_{b,bright} - L_{b,dark}) \tag{8}$$

$$L_{pb} = L_{b,dark} - RF_{b,dark}/m_b \tag{9}$$

However, the establishment of objects within every pixel image that have reliable, known reflectance factors, i.e., the establishment of calibration targets in an AOI, is time consuming and expensive.

The process utilizes the radiance image itself rather than any pre-established calibration targets in an AOI to determine $m_b$ and $L_{pb}$. To elaborate, with respect to determining $L_{pb}$, the radiance image produced according to equation (2) for an AOI almost always includes a pixel where the $RF_b$ is effectively zero or a feature with a known $RF_b$ at or about zero. Moreover, the smaller the resolution element (i.e., the smaller the area represented by a pixel), the greater the likelihood that there will be pixels with an $RF_b$ of effectively zero (shaded). The radiance image can be analyzed to identify a pixel or pixels that each have an $RF_b$ of effectively zero. Such analysis can be performed with a raster histogram tool in a GIS software package. FIG. 5 illustrates a radiance image with a pixel that has an $L_b$ with a value of 296 and a histogram for the radiance image that indicates that the lowest $L_b$ in the radiance image is 293. Consequently, the pixel that has an $L_b$ with a value of 296 is a good candidate for representing $L_{pb}$ within the image, i.e., the radiance attributable to the scattering of electromagnetic radiation by gases and other materials in the atmosphere between the sensor and the surface of the earth. An example of a feature with a known $RF_b$ is non-turbid, deep open water, which has a known $RF_b$ of nearly zero in the near infra-red (NIR) band.

For the pixel of the radiance image that is identified as having an $RF_b$ of 0 or approximately 0, equation (9) simplifies to:

$$L_{pb} = L_{b,dark} \tag{10}$$

At this point, the value for $L_{pb}$ has been determined. Further, the value of $L_{pb}$ is applicable to the bands of interest.

Rearranging equation (7A) yields an expression for $m_b$ of:

$$m_b = RF_{b,bright}/(L_{b,bright} - L_{pb}) \quad (11)$$

Consequently, since $L_{pb}$ is known from the radiance image (e.g. 296 in FIG. 5) and $L_{b,bright}$ will be known once a bright pixel is identified, $m_b$ can be determined if an object within the AOI can be identified with a known value for $RF_{b,bright}$. The process endeavors to identify for each band of interest an object that normally occurs in the agricultural AOIs that has a known or determinable $RF_{b,bright}$. Objects that meet this criteria may vary depending on the band of interest. For example, for the NIR band, dense herbaceous green vegetation (an agricultural scene-object) has a known reflectance factor of approximately 0.60. Consequently, for the NIR band, a pixel associated with dense herbaceous green vegetation is identified and the Lb,bright value for the pixel is used to determine $m_4$ under equation (11). With respect to the blue, green and red light bands, as well as the NIR band, it has been found that dry, bare, agricultural soil, another agricultural scene-object, is a reasonably bright object. However, the $RF_b$ for dry, bare, agricultural soil is not fixed. In general, agricultural scene-objects are objects that relate either to the crop vegetation or the soil associated with crop field.

To address the variable nature of the $RF_b$ for dry, bare, agricultural soil, a Line of Soils approach is employed. Specifically, there is a linear relationship between NIR reflectance factor of dry, bare, agricultural soils relative to red-light (RL) reflectance factor for the same soils that is expressed as:

$$RF_{nir,bas} = b_{nir,r1} + s_{nir,r1} RF_{r1,bas} \quad (12)$$

where the subscript bas refers to bare agricultural soil, $b_{nir,r1}$ is the intercept of the Line of Soils (i.e., the value of $RF_{nir}$ where $RF_{r1} = 0$ in the NIR versus RL feature space plot), and $S_{nir,r1}$ is the slope of the Line of Soils (in NIR versus R1 feature space).

The Line of Soils in each of the three 2-space plots involving band 4 (i.e., the NIR band) are as follows:

$$RF_{4,bas} = b_{43} + s_{43} RF_{3,bas} \quad (13)$$

$$RF_{4,bas} = b_{42} + s_{42} RF_{2,bas} \quad (14)$$

$$RF_{4,bas} = b_{41} + s_{41} RF_{1,bas} \quad (15)$$

Once a pixel for bright, dry, bare, agricultural soil has been identified, the $RF_{4,bas}$ for the pixel is calculated using equation (7A). The calculation of the $RF_{3,bas}$ utilizes the following known values of $b_{43}$ and $s_{43}$:

$$b_{43} = 0.0; \text{ and} \quad (16)$$

$$s_{43} = 1.1521 \quad (17)$$

These values may vary from one area to another. Further, these values vary based on the specific wavelengths and bandwidths of the NIR and RL bands employed. Consequently, these values are subject to modification. The values used for $b_{42}$, $s_{42}$, $b_{41}$ and $s_{41}$ are:

$$b_{42} = 0.0 \quad (18)$$

$$s_{42} = 1.333 \quad (19)$$

$$b_{41} = 0.0 \quad (20)$$

$$s_{41} = 1.6667 \quad (21)$$

These values are also subject to modification or refinement depending upon the situation. Based upon the substitution of the values for $RF_{4,bas}$, $b_{43}$ and $s_{43}$ into equation (13), the value for $RF_{3,bas}$ is:

$$RF_{3,bas} = RF_{4,bas}/1.1521 \quad (22)$$

The value of $m_3$ (i.e., the value of m for the red light band) is then calculated as:

$$m_3 = RF_{3,bas}/(L_{3,bas} = L_{p3}) \quad (23)$$

Similarly, the values for $m_2$ and $m_1$ are calculated. At this point, the values for $L_{pb}$ and $m_b$ in equation (7A) have been determined for each band of interest. As a consequence, the values for RF for each pixel for each band in the radiance image of the AOI is determined to produce a reflectance factor image for each band.

If the RF for dense herbaceous green vegetation in a particular scene is not approximately 0.60, errors in the estimates of m for the bands may result. In such a case, the calibration parameters $L_{pb}$ and $m_b$ may be determined by other methods. One method, involves the use of non-agricultural objects in a scene in which the reflectance of the object is substantially constant, such as airport runways, a flat roof on a building and the like. If the scene has been previously imaged, then a reflectance factor estimate exists that can be used in subsequent images to determine reflectance values if the RF for dense herbaceous green vegetation in the subsequent image is subject to question. Another method involves the use of calibration targets in the scene or other field measurements. Such an approach, in many cases, is not cost effective and care must be taken to use measurements at the same time that the raw image data is produced and to account for solar illumination angles, observation angles etc.

One or a combination of the reflectance factor images for the blue band (1), green band (2), red band (3) and NIR band (4) are used to produce an pixel map or image with agricultural information for the AOI. One type of pixel image or map that is produced from the reflectance factor images is a calibrated green vegetation index (GVI) map that is indicative of the vegetation canopy in the AOI. The equation for calculating the GVI based on RF values is:

$$GVI = (RF_4^* - RF_3^*)(1+L)F/(RF_4^* + RF_3^* + L) \quad (24)$$

where $RF_4^* = RF_4 - b_{43}$; $\quad (25)$ $$RF_3^* = s_{43} RF_3; \quad (26)$$

$$L = 0.5; \text{ and} \quad (27)$$

$$F = 136. \quad (28)$$

The value of F is selected so that the value of GVI is about 100 when RF4 is 0.60 and RF3 is 0.03. The parameter L is the soil adjustment coefficient. This results in GVI having a range of values from 0 to 100. A different range of values is also feasible by changing the value of F. The value of L, if the need arises, can also be changed. The values in the relevant GVI range are mapped to a color palette. In one embodiment, the lower values in the range are mapped to shades of browns, the upper values in the range are mapped to greens, and values in between the two extremes are mapped to other colors. It should be appreciated that the map can be a print out of the values for each pixel. However, such maps are typically more difficult to read than a map that maps the values to color. It should be appreciated that raw image data values or radiance values could be applied to equation (24) if desired.

The GVI is believed to address certain deficiencies in the Normalized Difference Vegetation Index (NDVI) and Soil Adjusted Vegetation Index (SAVI). Namely, under the NDVI and SAVI approaches the index value is only zero if $RF_4$ is equal to $RF_3$. This wrongly implies that the Line of Soils in $RF_4$ versus $RF_3$ space runs from (0,0) along a linear diagonal line of that space. In addition, NDVI is undefined when both $RF_4$ and $RF_3$ are equal to zero. NDVI is also highly sensitive to errors in $RF_4$ or $RF_3$ when the values are near zero. The NDVI also reaches a maximum value or saturates when the green vegetation reaches 100% ground cover. As a consequence, the NDVI is largely incapable of giving any indication of the biomass that is produced after the vegetation reaches full cover. The Transformed SAVI (TSAVI) approach accounts for the fact that the actual Line of Soils in $RF_4$ versus $RF_3$ space is given by a straight line that has a slope and intercept like that of equation (13). The approach represented by equations (24), (25), (26), (27) and (28) is capable of accounting for the case in which the Line of Soils has a slope different than 1 and an intercept different than (0,0).

Another type of pixel image or map that is or can be produced is a GVI change map that reflects the changes in the GVI pixel images relating to two different times. Typically, the requester desires the GVI change map to show the changes in GVI between two consecutive times when raw image data was obtained and from which a GVI map could be generated. However, if desired, a GVI change map showing the change in GVI between two, non-consecutive times can also be produced (i.e., when there are one or more times on which raw image data was obtained that are between the two times of interest). It should be appreciated that a GVI change map can be generated at any time provided that GVI data is available or can be produced for two different times. Typically, the GVI change map reflects the change in GVI between two times that are within one week of one another and more typically within three or four days of one another. In one embodiment, the raw image data for producing GVI images that are spaced four days from one another is accomplished by the use of a constellation of satellites with the satellites having orbit that result in one of the satellite passing over a specific AOI every four days. If desired GVI change maps can be produced that use data for times that are more closely spaced in time. It should also be appreciated that images produced by other remote sensing platforms or combinations of such platforms are also feasible. It has been found that producing GVI change maps using GVI data that is three to four days apart and providing the GVI change map to the requester within a few days of the end of the three or four day period provides the requester, especially when the requester is a farmer, with sufficient notice of changes in GVI to take appropriate action. In one embodiment, the GVI change data is mapped according to a scale that extends from 0 to 200. A value of 100 indicates that there was no change in GVI between the two times that GVI pixel maps that are being used to generate the GVI change map were generated. A value of 200 reflects the maximum increase in GVI between the two times, and a value of 0 reflects the maximum decrease in GVI between the two times. The scale is, in turn mapped into a color palette. In one embodiment, GVI change values between 0 and 94 are mapped to shades of red and yellow; a GVI change value of 95–105 is mapped to white; and GVI change values between 106 and 200 are mapped to shades of blue and green.

Another type of pixel image or map that is or can be produced from the reflectance factor images is a soil zone index (SZI) map that is indicative of differences in soil properties. If the GVI pixel map is generated, the equation for determining the SZI is:

$$SZI=250[sqrt((RF_3*+L/2)^2+(RF_4*+L/2)^2)-0.35] \qquad (29)$$

In practice, the range of SZI extends from 0 to 100. Low values of SZI (0–16) are associated with dark areas that are in shadows; values of SZI near 17 are associated with wet soils, silty loam soils, and/or soils having high organic matters content; and values of SZI near 100 are indicative of dry soils with sandy textures and low in organic content. The SZI values are mapped to a color palette to produce a colorized SZI pixel map. A different scale is also feasible and can be realized by changing the multiplication constant in equation (29). It should be appreciated that the map can be a print out of the values for each pixel. However, such maps are typically more difficult to read than a map that maps the values to color. It should also be appreciated that raw image data values or radiance values can be applied to equation (29) if desired.

The reflectance factor data, while discussed hereinabove with respect to the production of a GVI map, is also capable of being applied to known vegetation indexes, such as the Difference Green Vegetation Index (DGVI), Perpendicular Green Vegetation Index (PGVI), Normalized Difference Vegetation Index (NDVI), Simple Ratio Vegetation Index (SRVI), Infrared Percentage Vegetation Index (IRPVI), Soil Adjusted Vegetation Index (SAVI), Transformed Soil Adjusted Vegetation Index (TSAVI), Modified SAVI (MASVI), and MSAVI2. Moreover, the reflectance factor data is capable of being used in the production of change maps for each of the indexes.

The reflectance factor date, while discussed hereinabove with respect to the production of an SZI map, is also capable of being applied to known soil indexes, such as the Soil Brightness Index (SBI).

Whatever agricultural information map is produced using the reflectance factor values is conveyed to the requester. In one embodiment, the map is transmitted to the requester by conveying the map over the Internet. Typically, the map is conveyed in a compressed format. Once received, the requester is able to produce an layered image of the AOI with the bottom most layer being the digital topographic map in which the AOI is located, the next layer being the vector polygon that defines the boundaries of the AOI, and the final layer being the agricultural information map that overlays the polygon defining the AOI. It is also possible to convey the agricultural information map to the requester in other ways. For instance, the agricultural information map can be recorded on a magnetic disk, CD, tape or other recording medium and mailed to the requester. If needed the recording medium can also include the digital topographic map and the vector polygon layers also. It is also possible to simply produce a hard copy of a composite map in which the agricultural information map overlays the relevant topographic map and vector polygon that defines the AOI and then mail the hardcopy the requester. The hard copy can also be faxed or otherwise electronically sent to the requester.

The embodiment of the invention described hereinabove is intended to explain the best mode known of practicing the invention and to enable others skilled in the art to utilize the invention.

What is claimed is:

1. A method for producing agricultural information on an area of interest comprising:

receiving map information that defines an agricultural area of interest for which agricultural information is desired;

receiving remote imaging data on the agricultural area of interest;

processing, using data related to an agricultural scene-object, said remote imaging data on the agricultural area of interest to produce reflectance factor data on the agricultural area of interest, wherein a reflectance factor for a band b is denoted as $RF_b$, where $RF_b=(L_b-L_{pb})m_b$ and $m_b=\pi/(E_b t_{sb} \cos\theta + E_{b,sky}) t_{0b}$; and using said reflectance factor data on the agricultural area of interest to produce a map for the agricultural area of interest that provides agricultural information.

2. A method, as claimed in claim 1, wherein:

said step of using includes producing a green vegetation index (GVI) map for the agricultural area of interest according to the following:

$$GVI=(RF_4^*-RF_3^*)(1+L)F/(RF_4^*+RF_3^*+L)$$

where
$RF_4^*=RF_4-b_{43}$;
$RF_3^*=s_{43} RF_3$;
F is a scaling factor, and L is a soil adjustment coefficient.

3. A method, as claimed in claim 2, wherein:

said step of using includes producing a change in GVI map based upon a first GVI map for a first time and a second GVI map for a second time that is different than said first time.

4. A method, as claimed in claim 3, wherein:

said first time is within one week of said second time.

5. A method, as claimed in claim 1, wherein:

said step of using includes using said reflectance factor data to produce a soil zone index (SZI) map for the agricultural area of interest according to the following:

$$SZI=x[sqrt((RF_3^*+L/2)^2+(RF_4^*+L/2)^2)-0.35]$$

where
$RF_4^*=RF_4-b_{43}$;
$RF_3^*=s_{43} RF_3$;
L is a soil adjustment coefficient and x is a scaling constant.

6. A method, as claimed in claim 5, wherein:

x has a value of 250.

7. A method, as claimed in claim 1, wherein:

said step of using includes producing a map for one of the following indexes: Difference Green Vegetation Index (DGVI), Perpendicular Green Vegetation Index (PGVI), Normalized Difference Vegetation Index (NDVI), Simple Ratio Vegetation Index (SRVI), Infrared Percentage Vegetation Index (IRPVI), Soil Adjusted Vegetation Index (SAVI), Transformed Soil Adjusted Vegetation Index (TSAVI), Modified SAVI (MSAVI), and MSAVI2.

8. A method, as claimed in claim 7, wherein:

said step of using includes producing a change map based upon a first map for a selected one of said indexes for a first time and a second map for the selected one of said indexes for a second time that is different than said first time.

9. A method, as claimed in claim 1, furthering comprising:

conveying said map on the agricultural area of interest to an entity that is interested in agricultural information on the agricultural area of interest.

10. A method for producing agricultural information on an area of interest comprising:

receiving map information that defines the agricultural area of interest for which agricultural information is desired;

receiving remote imaging data on the agricultural area of interest;

processing, using data related to an agricultural scene-object, said remote imaging data on the agricultural area of interest to produce reflectance factor data on the agricultural area of interest; and using said reflectance factor data on the agricultural area of interest to produce a green vegetation index (GVI) map for the agricultural area of interest according to the following:

$$GVI=(RF_4^*-RF_3^*)(1+L)F/(RF_4^*+RF_3^*+L)$$

where
$RF_4^*=RF_4-b_{43}$;
$RF_3^*=s_{43} RF_3$;
F is a scaling factor, and L is a soil adjustment coefficient.

11. A method, as claimed in claim 10, further comprising:

identifying said GVI map as a first GVI map that relates to a first time; and repeating said step of receiving, processing and using to produce a second GVI map for the agricultural area of interest that relates to a second time that is different than said first time.

12. A method, as claimed in claim 11, further comprising:

using said first GVI map and said second GVI map to produce a change in GVI map.

13. A method for producing agricultural information on an area of interest comprising:

receiving map information that defines an agricultural area of interest for which agricultural information is desired;

receiving remote imaging data on the agricultural area of interest;

processing, using data related to an agricultural scene-object, said remote imaging data on the agricultural area of interest to produce reflectance factor data on the agricultural area of interest; and using said reflectance factor data on the agricultural area of interest to produce a soil zone index (SZI) map for the agricultural area of interest according to the following:

$$SZI=x[sqrt((RF_3^*+L/2)^2+(RF_4^*+L/2)^2)-0.35]$$

where
$RF_4^*=RF_4-b_{43}$;
$RF_3^*=s_{43} RF_3$;
L is a soil adjustment coefficient and x is a scaling constant.

14. A method, as claimed in claim 13, further comprising:

using said reflectance factor data to produce a vegetation index map before using said reflectance data to produce said soil zone index map.

15. A method, as claimed in claim 14, wherein:

said vegetation index map is a green vegetation index map.

16. A method for producing agricultural information on an area of interest comprising:

receiving map information that defines an agricultural area of interest for which agricultural information is desired;

first receiving first remote imaging data on the agricultural area of interest for a first time;

first calibrating, using data related to an agricultural scene-object, said first remote imaging data on the agricultural area of interest to produce first reflectance factor data for said first time;

first using said first reflectance factor data to produce a first map according to a selected index;

second receiving second remote imaging data on the agricultural area of interest for a second time;

second calibrating, using data related to an agricultural scene-object, said second remote imaging data on the agricultural area of interest to produce second reflectance factor data for said second time;

second using said second reflectance factor data to produce a second map according to said selected index; and using said first map and said second map to produce a change map that shows the change in the index between said first time and said second time;

wherein a reflectance factor for a band b is denoted as $RF_b$, where $RF_b = (L_b - L_{pb}) m_b$ and $m_b = \pi/(E_b t_{sb} \cos\theta + E_{b,sky}) t_{0b}$.

17. A method, as claimed in claim 16, wherein:

said selected index is a green vegetation index (GVI) in which pixel values are determined according to the following:

$$GVI = (RF_4^* - RF_3^*)(1+L)F/(RF_4^* + RF_3^* + L)$$

where $RF_4^* = RF_4 - b_{43}$;

$RF_3^* = s_{43} RF_3$;

F is a scaling factor, and L is a soil adjustment coefficient.

18. A method for producing agricultural information on an area of interest comprising:

receiving map information that defines an agricultural area of interest for which agricultural information is desired;

receiving remote imaging data on the agricultural area of interest;

calibrating said remote imaging data on the agricultural area of interest to produce calibrated data; and using said calibrated data on the agricultural area of interest to produce a green vegetation index (GVI) map for the agricultural area of interest according to the following:

$$GVI = (RF_4^* - RF_3^*)(1+L)F/(RF_4^* + RF_3^* + L)$$

where $RF_4^* = RF_4 - b_{43}$;

$RF_3^* = s_{43} RF_3$;

F is a scaling factor, L is a soil adjustment coefficient, and RF stands for reflectance factor.

19. A method, as claimed in claim 18, wherein:

said step of calibrating includes using a value associated with a pixel that corresponds to an agricultural scene-object.

20. A method, as claimed in claim 19, wherein:

said agricultural scene object includes dense herbaceous green vegetation.

21. A method, as claimed in claim 19, wherein:

said agricultural scene object includes dry, bare, agricultural soil.

22. A method, as claimed in claim 18, wherein:

said step of calibrating does not include the use of a value associated with a pixel that corresponds to an agricultural scene-object.

23. A method, as claimed claim 18, wherein:

said step of calibrating includes using a calibration target.

24. A method, as claimed in claim 18, wherein:

said step of using includes producing a change map based upon differences between a first map for a first time and a second map for a second time that is different than said first time.

25. A method for producing agricultural information on an area of interest comprising:

receiving map information that defines an agricultural area of interest for which agricultural information is desired;

receiving remote imaging data on the agricultural area of interest; and using said remote imaging data on the agricultural area of interest to produce a green vegetation index (GVI) map for the agricultural area of interest according to the following:

$$GVI = (ID_4^* - ID_3^*)(1+L)F/(ID_4^* + ID_3^* + L)$$

where $ID_4^* = ID_4 - b_{43}$;

$ID_3^* = s_{43} ID_3$;

F is a scaling factor, L is a soil adjustment coefficient, and ID values are raw image data or radiance values.

26. A method for producing agricultural information on an area of interest comprising:

receiving map information that defines an agricultural area of interest for which agricultural information is desired;

receiving remote imaging data on the agricultural area of interest;

calibrating said remote imaging data on the agricultural area of interest to produce calibrated data; and using said calibrated data on the agricultural area of interest to produce a soil zone index (SZI) map for the agricultural area of interest according to the following:

$$SZI = x[sqrt((RF_3^* + L/2)^2 + (RF_4^* + L/2)^2) - 0.35]$$

where $RF_4^* = RF_4 - b_{43}$;

$RF_3^* = s_{43} RF_3$;

L is a soil adjustment coefficient and x is a scaling constant.

27. A method, as claimed in claim 26, wherein:

said step of calibrating includes using a value associated with a pixel that corresponds to an agricultural scene-object.

28. A method, as claimed in claim 26, wherein:

said step of calibrating does not include the use of a value associated with a pixel that corresponds to an agricultural scene-object.

29. A method for producing agricultural information on an area of interest comprising:

receiving map information that defines an agricultural area of interest for which agricultural information is desired;

receiving remote imaging data on the agricultural area of interest; and using said remote imaging data on the agricultural area of interest to produce a soil zone index (SZI) map for the agricultural area of interest according to the following:

$$SZI = x[sqrt((ID_3^* + L/2)^2 + (ID_4^* + L/2)^2) - 0.35]$$

where $ID_4^* = ID_4 - b_{43}$;

$ID_3^* = s_{43} ID_3$;

L is a soil adjustment coefficient, x is a scaling constant, and ID values are raw image data or radiance values.

30. A method for transporting agricultural information on an area of interest towards an interested entity comprising:
conveying, over a portion of a computer network, a map that provides agricultural information on the area of interest, the map including agricultural information that has been produced using reflectance factor data wherein a reflectance factor for a band b is denoted as $RF_b$, where $RF_b = (L_b - L_{pb})m_b$ and $m_b = \pi/(E_b t_{sb} \cos\theta + E_{b,sky}) t_{Ob}$, and one of the following: data related to an agricultural scene-object, a formula for producing a green vegetation index (GVI), and a formula for producing soil zone index (SZI).

31. A method, as claimed in claim 30, wherein:
said computer network includes the Internet.

* * * * *

UNITED STATES PATENT AND TRADEMARK OFFICE
CERTIFICATE OF CORRECTION

PATENT NO. : 7,068,816 B1
APPLICATION NO. : 10/047423
DATED : June 27, 2006
INVENTOR(S) : Knoblauch et al.

It is certified that error appears in the above-identified patent and that said Letters Patent is hereby corrected as shown below:

Page 2 of Title Page, second column, line 21, delete "Clarke, A Refined", and insert --Clark, "A, Refined--;

Column 8, line 9, delete "$m_3=RF_{3,bas}/(L_{3,bas}=L_{p3})$", and insert --$m_3=RF_{3,bas}/(L_{3,bas}-L_{p3})$--.

Signed and Sealed this

Second Day of January, 2007

JON W. DUDAS
*Director of the United States Patent and Trademark Office*